United States Patent
Van Vorhis et al.

(10) Patent No.: US 9,050,131 B2
(45) Date of Patent: Jun. 9, 2015

(54) FIBER OPTIC TRACKING SYSTEM AND METHOD FOR TRACKING A SUBSTANTIALLY RIGID OBJECT

(75) Inventors: Robert Van Vorhis, Davis, CA (US); Benny Hagag, Plantation, FL (US); Hyosig Kang, Weston, FL (US); Chris Lightcap, Ft. Lauderdale, FL (US); Rony Abovitz, Hollywood, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 704 days.

(21) Appl. No.: 12/486,382

(22) Filed: Jun. 17, 2009

(65) Prior Publication Data
US 2009/0314925 A1 Dec. 24, 2009

Related U.S. Application Data

(60) Provisional application No. 61/132,446, filed on Jun. 18, 2008.

(51) Int. Cl.
*G01D 5/353* (2006.01)
*G01V 8/20* (2006.01)
(Continued)

(52) U.S. Cl.
CPC ......... *A61B 19/5244* (2013.01); *A61B 19/2203* (2013.01); *A61B 2019/467* (2013.01);
(Continued)

(58) Field of Classification Search
CPC .. G02B 6/02; G02B 6/02057; G02B 6/02066; G02B 6/02071; G02B 6/02076; G02B 6/0208; G02B 6/02085; G02B 2006/0209; G02B 6/02095; G02B 6/021; G02B 6/02114; G02B 6/028; G01D 5/268; G01D 5/32; G01D 5/34; G01D 5/353; G01D 5/35303; G01D 5/35316

USPC .................. 250/216, 227.28, 227.27, 227.11, 250/227.14, 227.15–227.21; 318/560, 318/568.11, 568.16; 901/1, 2, 14–18, 901/27–29, 46, 47; 348/94, 95; 385/12, 13, 385/4, 5, 10; 600/101, 424, 407, 109; 606/15, 16, 1, 10; 359/34

See application file for complete search history.

(56) References Cited

U.S. PATENT DOCUMENTS 5,798,521 A 8/1998 Froggatt
6,256,090 B1 * 7/2001 Chen et al. .................... 356/73.1
(Continued)

FOREIGN PATENT DOCUMENTS

WO WO 2008/097540 A2 8/2008
WO WO 2009/023801 A1 2/2009

OTHER PUBLICATIONS

Challis, John H., "A Procedure for Determining Rigid Body Transformation Parameters," J. Biomechanics, vol. 28, No. 6, (1995), p. 733-737.
(Continued)

Primary Examiner — Pascal M Bui Pho
(74) Attorney, Agent, or Firm — Foley & Lardner LLP

(57) ABSTRACT

A fiber optic tracking system for tracking substantially rigid object(s) is described. The fiber optic tracking system includes a light source, an optical fiber having a sensing component configured to modify optical signals from the light source, the optical fiber being configured to attach to the substantially rigid object, a detection unit arranged to receive the modified optical signals from the sensing component, and a calculation unit configured to determine a pose of the substantially rigid object in six degrees of freedom based on the modified optical signals.

25 Claims, 11 Drawing Sheets

(51) Int. Cl.
*A61B 19/00* (2006.01)
*G02B 6/02* (2006.01)

(52) U.S. Cl.
CPC . *A61B2019/5255* (2013.01); *A61B 2019/5259* (2013.01); *A61B 2019/5483* (2013.01); *G02B 6/02042* (2013.01); *G02B 6/02057* (2013.01)

(56) References Cited

U.S. PATENT DOCUMENTS

| | | | |
|---|---|---|---|
| 6,322,567 | B1 | 11/2001 | Mittelstadt et al. |
| 6,470,205 | B2 * | 10/2002 | Bosselmann et al. ......... 600/424 |
| 6,471,710 | B1 * | 10/2002 | Bucholtz ....................... 606/130 |
| 7,930,065 | B2 * | 4/2011 | Larkin et al. .................. 700/245 |
| 2001/0021843 | A1 | 9/2001 | Bosselmann et al. |
| 2002/0052546 | A1 | 5/2002 | Frantz et al. |
| 2004/0165810 | A1 | 8/2004 | Fujita |
| 2005/0203383 | A1 | 9/2005 | Moctezuma de la Barrera et al. |
| 2005/0222554 | A1 | 10/2005 | Wallace et al. |
| 2006/0013523 | A1 | 1/2006 | Childers et al. |
| 2006/0142657 | A1 | 6/2006 | Quaid et al. |
| 2007/0043338 | A1 | 2/2007 | Moll et al. |
| 2007/0065077 | A1 * | 3/2007 | Childers et al. ................. 385/37 |
| 2007/0156019 | A1 | 7/2007 | Larkin et al. |
| 2007/0265503 | A1 | 11/2007 | Schlesinger et al. |
| 2008/0071140 | A1 | 3/2008 | Gattani et al. |
| 2008/0097155 | A1 | 4/2008 | Gattani et al. |
| 2008/0218770 | A1 | 9/2008 | Moll et al. |
| 2008/0285909 | A1 | 11/2008 | Younge et al. |
| 2009/0076476 | A1 | 3/2009 | Barbagli et al. |
| 2009/0123111 | A1 | 5/2009 | Udd |
| 2009/0137952 | A1 | 5/2009 | Ramamurthy et al. |
| 2009/0138025 | A1 | 5/2009 | Stahler et al. |

OTHER PUBLICATIONS

Veldpaus, F.E. et al, "A Least-Squares Algorithm for the Equiform Transformation from Spatial Marker Co-ordinates," J. Biomechanics, vol. 21, No. 1, (1988), pp. 44-54.
Andreas Othonos, et al. "Fiber Bragg Gratings, Fundamentals and Applications in Telecommunications and Sensing," Artech House Optoelectronics Library, (1999), pp. 301-303.
U.S. Appl. No. 60/788,176, filed Mar. 31, 2006, King T. St. John.
U.S. Appl. No. 60/899,048, filed Feb. 2, 2007, Federic H. Moll.
U.S. Appl. No. 60/588,336, filed Jul. 16, 2004, Brooks A. Childers.
U.S. Appl. No. 60/785,001, filed Mar. 22, 2006, King T. St. John.
U.S. Appl. No. 60/900,584, filed Feb. 8, 2007, Frederic H. Moll.
U.S. Appl. No. 60/964,773, filed Aug. 14, 2007, B. S. Ramamurthy.
U.S. Appl. No. 61/003,008, filed Nov. 13, 2007, Eric Udd.
International Search Report for App No. PCT/US2009/047624 dated Dec. 8, 2009.
Written Opinion for App. No. PCT/US2009/047624 dated Dec. 8, 2009.
Reply to Written Opinion for App. No. PCT/US2009/047624 dated Apr. 5, 2010.
International Preliminary Report on Patentability for App. No. PCT/US2009/047624 dated Sep. 10, 2010.

* cited by examiner

FIBER OPTIC TRACKING SYSTEM AND METHOD FOR TRACKING A SUBSTANTIALLY RIGID OBJECT

CROSS-REFERENCE TO RELATED PATENT APPLICATIONS

This application claims priority from U.S. Provisional Patent Application Ser. No. 61/132,446, filed Jun. 18, 2008, which is incorporated herein by reference in its entirety.

BACKGROUND OF THE INVENTION

1. Field of Invention

The invention relates to a fiber optic tracking system for tracking a substantially rigid object and a method for tracking a substantially rigid object using a fiber optic tracking system.

2. Description of Related Art

It is often necessary to determine or track the position of an object. For example, computer assisted surgical systems have been developed that use robotic devices that are precise and can greatly improve surgical procedures. Proper performance of those devices requires the tracking of positions of objects, such as portions of the human anatomy, surgical instruments, and portions of the robotic device.

There are several conventional surgical navigation technologies that are used to track the positions of objects during surgical procedures. For example, infra red tracking technology has been developed and commercialized by Northern Digital Inc ("NDI"); and electro magnetic ("EM") tracking has been developed and commercialized by Visualization Technologies Inc. Additional efforts are currently being made towards the development of tracking technologies that utilize radio frequency ("RF") technology, ultrasonic technology, laser scanning devices, a 3D optical camera with triangulation capabilities, and combinations of some of the above referenced technologies. Disadvantages of such conventional surgical navigation technologies can include the failure to provide seamless integration; high accuracy; high sampling rate; robust tracking capability that is not easily affected by a surgical procedure or by the surgical workflow; and tracking of any combination of, for example, patient anatomy, surgical instruments, the surgical robotic arm, bone cutting instruments, and other objects.

A need exists for an improved surgical navigation technology that address issues such as the disadvantages of conventional surgical technologies noted above, which are listed merely as examples and not as requirements.

SUMMARY OF THE INVENTION

According to an aspect of the present invention, there is provided a fiber optic tracking system for tracking a substantially rigid object, comprising a light source, an optical fiber, a detection unit, and a calculation unit. The light source provides optical signals. The optical fiber has a sensing component configured to modify the optical signals from the light source and the optical fiber is configured to attach to the substantially rigid object. The detection unit is arranged to receive the modified optical signals from the sensing component. The calculation unit is configured to determine a pose of the substantially rigid object in six degrees of freedom based on the modified optical signals.

According to another aspect of the present invention, there is provided a method for tracking a substantially rigid object using a fiber optic tracking system. The method comprises providing a light source; attaching an optical fiber, having a sensing component configured to modify the optical signals from the light source, to the substantially rigid object; and determining a pose of the substantially rigid object in six degrees of freedom based on the modified optical signals.

According to yet another aspect of the present invention, there is provided a fiber optic tracking system for transducing the angle between a first substantially rigid object and a second substantially rigid object constrained to move relative to the first substantially rigid object in one-dimension defined by the angle, comprising a light source, an optical fiber, a detection unit, and a calculation unit. The light source provides optical signals. The optical fiber has a first sensing component and a second sensing component. The first sensing component is configured to modify optical signals from the light source to provide first modified optical signals and the second sensing component is configured to modify optical signals from the light source to provide second modified optical signals. The optical fiber is configured to attach to the first substantially rigid object such that the first sensing component is fixed relative to the first substantially rigid object and to attach to the second substantially rigid object such that the second sensing component is fixed relative to the second substantially rigid object. The detection unit is arranged to receive the first and second modified optical signals from the first and second sensing components. The calculation unit is configured to determine the angle based on the first and second modified optical signals.

BRIEF DESCRIPTION OF THE DRAWINGS

The accompanying drawings, which are incorporated and constitute a part of this specification, illustrate embodiments of the invention and together with the description serve to explain aspects of the invention.

DETAILED DESCRIPTION OF THE PREFERRED EMBODIMENTS

Figure 1:
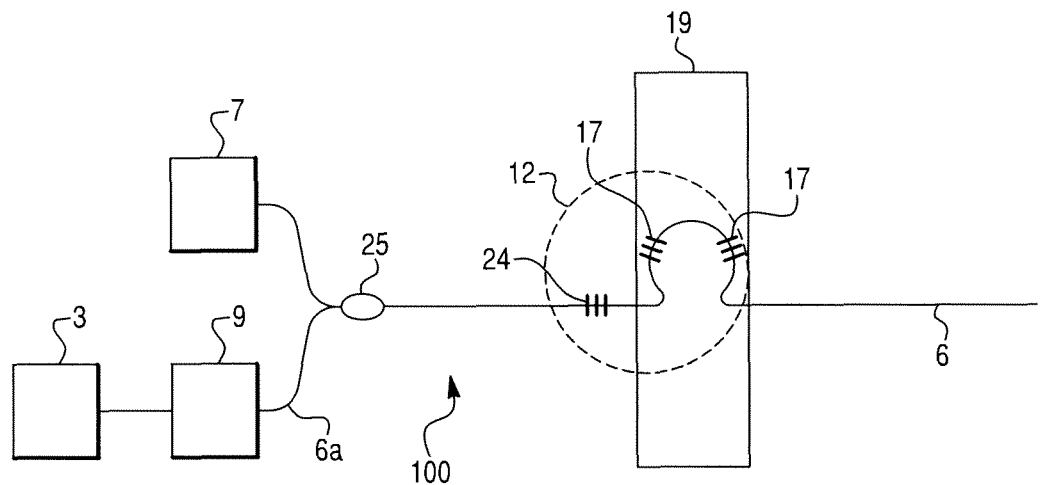
FIG. 1 is a schematic view of a fiber optic tracking system tracking a single object according to an embodiment of the invention.

Presently preferred embodiments of the invention are illustrated in the drawings. An effort has been made to use the same or like reference numbers throughout the drawings to refer to the same or like parts. Although the specification refers primarily to surgical systems, it should be understood that the subject matter described herein is applicable to the tracking of objects in general.

Overview of the Fiber Optic Tracking System

Figure 2:
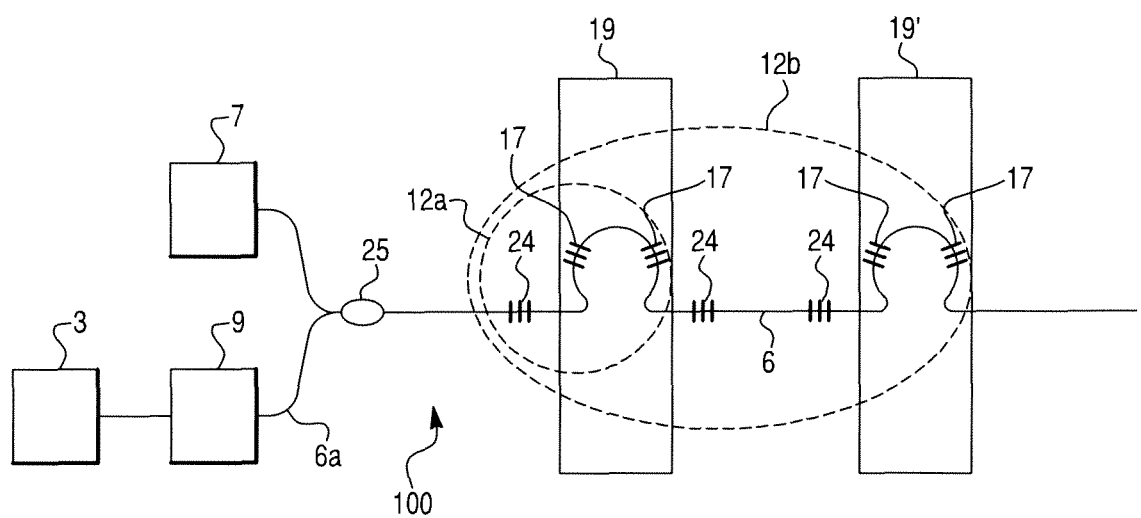
FIG. 2 is a schematic view of a fiber optic tracking system tracking multiple objects according to another embodiment of the invention.

Referring to FIGS. 1 and 2, a fiber optic tracking system 100 according to an embodiment of the present invention preferably includes a light source 7, an optical fiber 6 with at least one sensing component 12, a detection unit 9, and a calculation unit 3. In this application, the reference numeral 12 is used generically to refer to a sensing component, and the reference characters 12a, 12b, 12c, 12', etc. are used to distinguish between specific sensing components. Each of these portions or components of the fiber optic tracking system 100 will be explained in more detail below.

The fiber optic tracking system 100 may be used to track one or more substantially rigid objects 19, 19'. In the context of the present invention, an object can be considered substantially rigid if the relative position of any two points on the object remains constant in a manner sufficient for the intended use when the object is subjected to forces incurred during typical use. In simplified terms, the fiber optic tracking system 100 can be configured to use the sensing component 12, including sensing points 17, 24 along the optical fiber 6, to determine, for example, the position of at least one such sensing point 17 to determine or estimate the shape of the optical fiber 6, the shape of portions thereof, and/or the location of points thereon, and use that information to track the one or more substantially rigid objects 19, 19'. The sensing points preferably are large in number and closely distributed in order to increase the accuracy of the determination of the shape of the optical fiber 6, the shape of portions thereof, and/or the location of points thereon. Therefore, in general, there preferably will be many more sensing points than shown in FIGS. 1 and 2. For ease of illustration, however, a smaller number of sensing points than likely would be used in practice is shown in the figures. Specific techniques for performing the tracking will be explained in more detail below.

As shown in FIG. 1, the optical fiber 6 may be connected to a single substantially rigid object 19 to allow the fiber optic tracking system 100 to determine the position and/or orientation of that substantially rigid object 19. In this preferred configuration, a single sensing component 12 is associated with the substantially rigid object 19. Alternatively, as shown in FIG. 2, the optical fiber 6 may be connected to multiple substantially rigid objects 19, 19' (two objects in this instance) to allow the fiber optic tracking system 100 to determine the position and/or orientation of each of those substantially rigid objects 19, 19'. In the embodiment shown in FIG. 2, the optical fiber 6 preferably includes two sensing components 12a, and 12b, corresponding respectively to substantially rigid objects 19 and 19'. In both of the embodiments of FIGS. 1 and 2, though not shown, it is to be understood that multiple (two or more) sensing components may be provided on each substantially rigid object.

Figure 3:
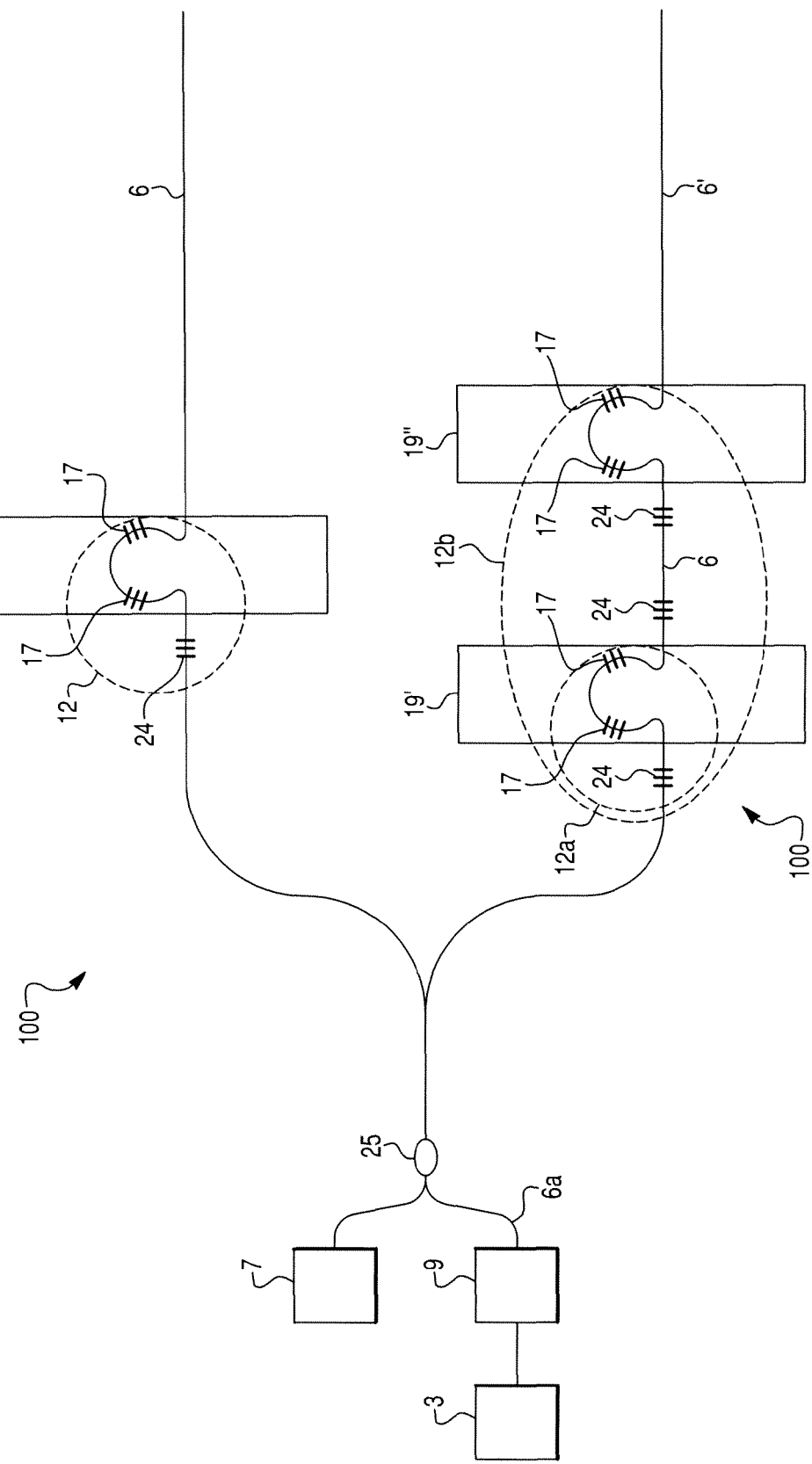
FIG. 3 is a schematic view of a fiber optic tracking system using multiple optical fibers to track multiple objects according to another embodiment of the invention.

The fiber optic tracking system 100 also may include multiple (two or more) optical fibers 6, 6'. The fiber optic tracking system 100 shown in FIG. 2 utilizes only one optical fiber 6 and obtains information from each of the sensing components 12 associated with the two substantially rigid objects 19, 19' for tracking purposes. However, as shown in the example of FIG. 3, the fiber optic tracking system 100 may utilize two or more optical fibers 6, 6'. One optical fiber 6 can obtain information from the sensing component 12 associated with one substantially rigid object 19 and another optical fiber 6' can obtain information from each of the sensing components 12a and 12b associated with two other substantially rigid objects 19' and 19" for tracking purposes.

Figure 4:
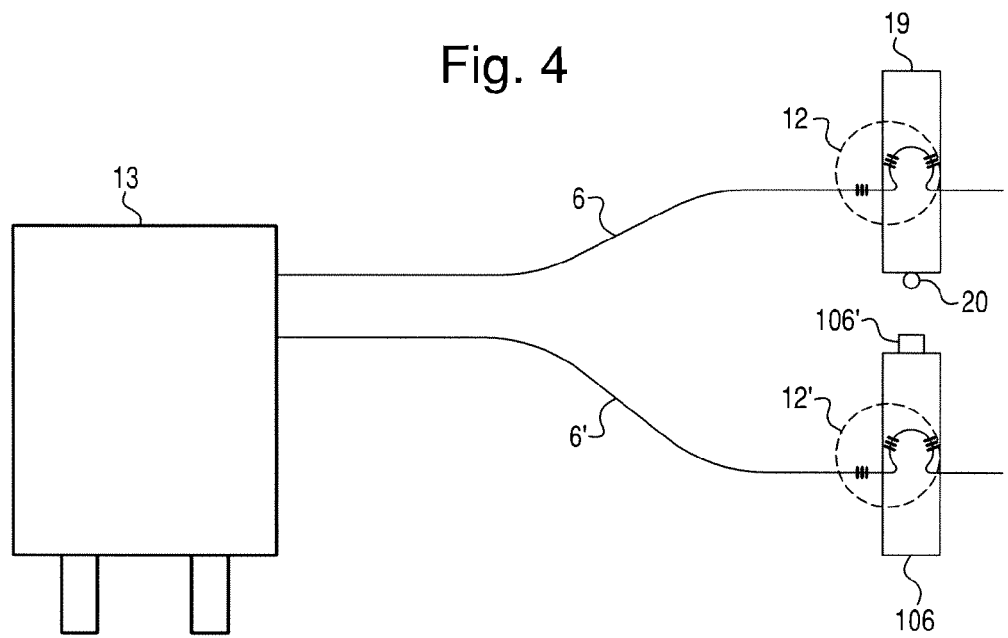
FIG. 4 is a schematic view of a robotic surgical device having a fiber optic tracking system according to yet another embodiment of the invention.
Figure 5:
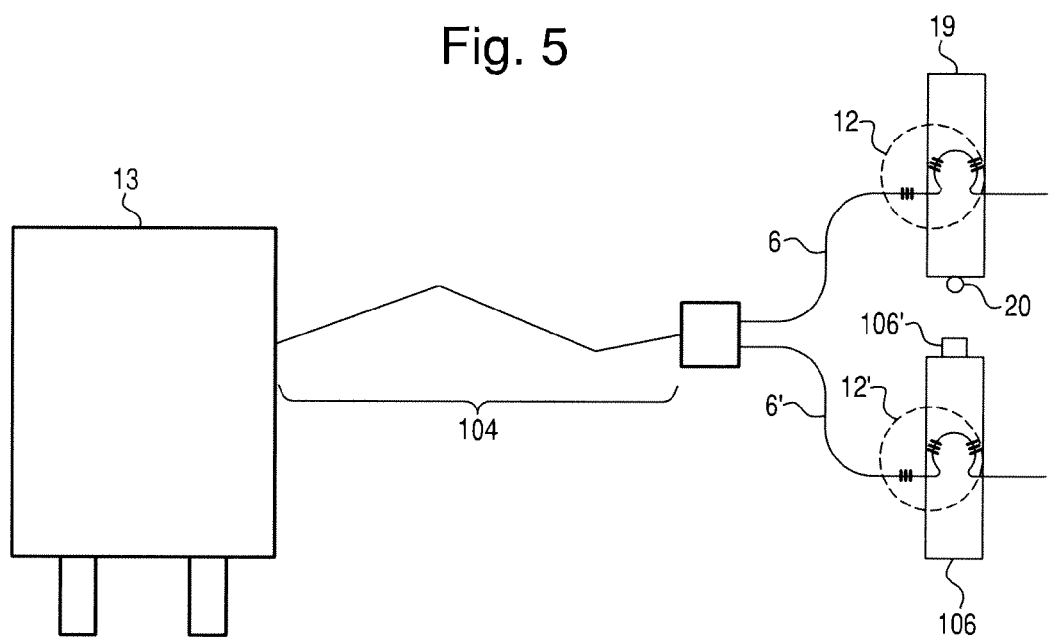
FIG. 5 is a schematic view of a robotic surgical device having both a fiber optic tracking system and a mechanical tracking system according to an embodiment of the invention.

As illustrated in FIGS. 4 and 5, tracking of a substantially rigid object 19 may be accomplished using the fiber optic tracking system 100 alone (FIG. 4) or in combination with other tracking systems, such as a mechanical tracking system 104 (FIG. 5). FIGS. 4 and 5 are schematic representations in which the light source 7, detection unit 9, and calculation unit 3 are not shown, but it is to be understood that they are present.

With reference to FIG. 4, the optical fiber 6 is connected to the substantially rigid object 19 to perform tracking. The optical fiber 6 also can be connected to an object, such as a robotic device 13. The optical fiber 6 can be connected to one or more locations on the robotic device 13, such as a base, an arm, a manipulator, a tool, etc. In this configuration, the fiber optic tracking system 100 alone can facilitate tracking of the substantially rigid object 19.

With reference to FIG. 5, the optical fiber 6 again is connected to the substantially rigid object 19. In this embodiment, however, the optical fiber 6 also is connected to another tracking system, such as a mechanical tracking system 104, which in turn is connected to the robotic device 13. Information from both the fiber optic tracking system 100 and the mechanical tracking system 104 can be used to track the substantially rigid object 19. The mechanical tracking system 104 may be any suitable tracking system. For example, the mechanical tracking system may be a passive articulated mechanical arm, as described in U.S. Pat. No. 6,322,567, which is incorporated herein by reference in its entirety. In such a configuration, the mechanical tracking system 104 can be used, for example, for positioning over long distances (e.g., on the order of meters), and the fiber optic tracking system 100 can be used, for example, for positioning over short distances (e.g., on the order of centimeters). The mechanical tracking system 104 may be substantially constantly movable. Alternatively, the passive mechanical arm that supports the base of the optical fiber can be locked into a particular location to serve as a reference point. In lieu of a mechanical tracking system, the long distance portion of the tracking may be accomplished by another type of tracking system, such as an optical, electromagnetic, or radio-frequency tracking system.

A Preferred Use of the Fiber Optic Tracking System

Figure 6:
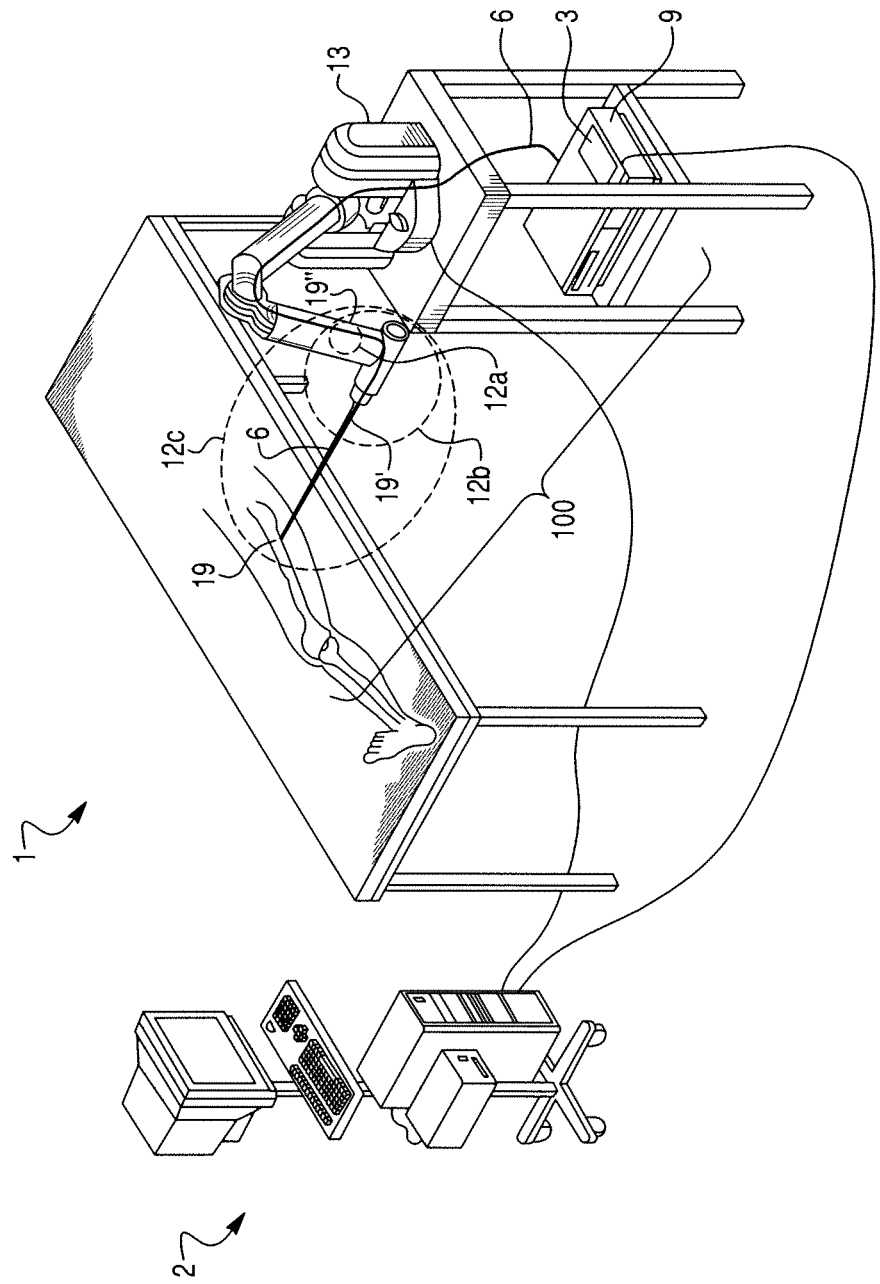
FIG. 6 is a perspective view of a surgical system including a fiber optic tracking system according to an embodiment of the invention.

In a preferred embodiment, the fiber optic tracking system 100 can be used in a computer assisted surgical system 1. As shown in FIG. 6, the surgical system 1 may include, in addition to the fiber optic tracking system 100, a robotic surgical device 13, including a computer system 2, to enable a surgeon to execute a surgical procedure. In one embodiment, the surgical device 13 and computer system 2 comprise an interactive robotic surgical system as disclosed in U.S. Pub. No. 2006/0142657, published Jun. 29, 2006, which is hereby incorporated by reference in its entirety. Alternatively, the robotic surgical device 13 and computer system 2 may comprise a teleoperated robotic surgical system or an autonomous robotic surgical system. The fiber optic tracking system 100 is not limited to use with a robotic surgical system but can be used with any surgical system in which tracking of anatomy, surgical instruments, and/or portions of the surgical system are required.

In this configuration, the fiber optic tracking system 100 can be used to track one or more substantially rigid objects 19, 19', 19" of the surgical system 1 and/or the patient, the location of which is required or preferred to be known to execute a surgical procedure. For example, the substantially rigid object 19 may include a portion of the human body or anatomy (e.g., a bone), the substantially rigid object 19' may include a cutting tool, and the substantially rigid object 19" may include a portion of the robotic surgical device 13, such as a robot arm. The substantially rigid object also could be other components, such as other tools/instruments, implants/prosthetic devices, work pieces, and other components. The optical fiber 6 includes sensing components 12a, 12b, and 12c located, respectively, on the substantially rigid objects 19, 19', and 19" to assist in determining the pose (i.e., position and/or orientation) of the substantially rigid objects 19, 19', and 19". The poses of these substantially rigid objects 19, 19', 19" are used by the surgical system for proper computer assistance and execution of the surgical procedure.

Referring back to FIGS. 4 and 5, in surgical and other environments, the fiber optic tracking system 100 can be configured to perform registration. For example, the tracking system 100 can be used to register (map or associate) coordinates in one space to those in another to determine spatial alignment or correspondence (e.g., using a conventional coordinate transform process). For example, the tracking system 100 can be used to register the substantially rigid object 19 (e.g., a bone) in physical space to an image of the substantially rigid object 19 in image space. The tracking system 100 can also be used to register the location of the sensing component 12 on the substantially rigid object 19 and the location of a point of interest 20 (or multiple points of interest) on the substantially rigid object 19. This registration may be used, for example, to register points of interest on the end of a patient's bone relative to the location of the sensing component attached to that bone, preoperatively and/or intraoperatively, to determine the spatial (or geometric) relationship between the sensing component 12 attached to the bone and the points of interest on the bone. Once the spatial relationship is known, movement of the sensing component 12 can be correlated to movement of the points of interest. Registration is performed using, for example, a probe 106, which may be any conventional device that can contact the surface of the substantially rigid object 19 at the points of interest 20. For example, the probe 106 can be a device with a blunt tip 106' at one end, where the blunt tip 106' is moved by an operator to contact the surface of the substantially rigid object 19. By contacting points of interest 20 on the substantially rigid object 19 with the blunt tip 106' of the probe 106 and tracking the blunt tip 106', the surgical system 1 can determine the location of those points of interest 20 in physical space. Knowing the physical space locations of the points of interest 20 and the sensing component 12 attached to the substantially rigid object 19, the surgical system 1 can determine the relative spatial relationship between the sensing component 12 of the substantially rigid object 19 and the points of interest. To perform such registration, however, the location of the blunt tip 106' of the probe 106 as the blunt tip 106' contacts the points of interest 20 also must be determined (e.g., tracked). This can be accomplished through the use of a sensing component 12' of another optical fiber 6' in the fiber optic tracking system 100. The sensing component 12' can be collocated, for example, with the blunt tip 106' of the probe 106. Alternatively, the sensing component 12' can be located elsewhere on the probe 106 such that the sensing component 12' has a known fixed spatial relationship to the blunt tip 106'. If the spatial relationship is not known, the spatial relationship can be determined by registering the location of the blunt tip 106' to the location of the sensing component 12' on the probe 106. Once the spatial relationship is known, the location of the blunt tip 106' can be determined based on the location of the sensing component 12'.

It is to be understood that the above-described registration (e.g., between the locations of the points of interest 20 and the location of the sensing component 12 attached to the substantially rigid object 19, between the substantially rigid object 19 and an image of the substantially rigid object, etc.) do not require use of the probe 106 and/or the fiber optic tracking system 100. For example, instead of performing registration using the probe 106 and the fiber optic tracking system 100, it is possible to use a probe that is tracked by a conventional optical or mechanical tracking system. It is also possible to use a conventional registration process with an external device, such as a radiographic, MR, ultrasound, or other medical imaging device. Moreover, a coordinate measuring machine or digitizing arm may be used to register the location of the blunt tip 106' relative to the location of the sensing component 12' on the probe 106, if required. Alternatively, the location of the sensing component 12' relative to the probe tip 106' may be obtained by moving the probe 106 such that the probe tip 106' remains at a given point, while the sensing component 12' moves along a surface of a virtual sphere with the sphere center being the given point. The probe tip 106' location can be estimated by fitting the collected point positions of the sensing component 12' to a sphere and solving for the radius and center of the sphere.

The components or portions of the fiber optic tracking system 100 will now be described in greater detail.

The Light Source

In the fiber optic tracking system 100, the light source 7 provides or emits optical signals that propagate through the optical fiber 6. Modifications by the optical fiber 6 of the light emitted from the light source 7 are used to determine the configuration of the optical fiber 6 and track the substantially rigid object(s) 19. Preferably, the light source 7 is a broadband light source or a tunable laser. For example, the light source 7 may be an LED, ELED, or SLD.

The Optical Fiber

The optical fiber 6 preferably is configured to act as a waveguide and guide light emitted from the light source 7. The light propagates along a core or cores of the optical fiber 6. The optical fiber 6 can have, for example, a tri-core configuration or a dual-core configuration. A fiber optic tracking system 100 also can be constructed using a plurality of single core fibers in place of a single multi-core fiber. For ease of description, the singular phrase optical fiber will be used herein to describe a plurality of single core fibers, in addition to describing a single multi-core fiber.

The optical fiber 6 includes sensing components 12, each of which is configured to modify light from the light source 7 (which is propagating through the optical fiber 6) to create a modified optical signal. This modification of the light can be used, as explained below, to track the location of all or portion(s) of the optical fiber 6, which in turn allows for the determination of the position and/or orientation of the substantially rigid object(s) 19.

Figure 7:
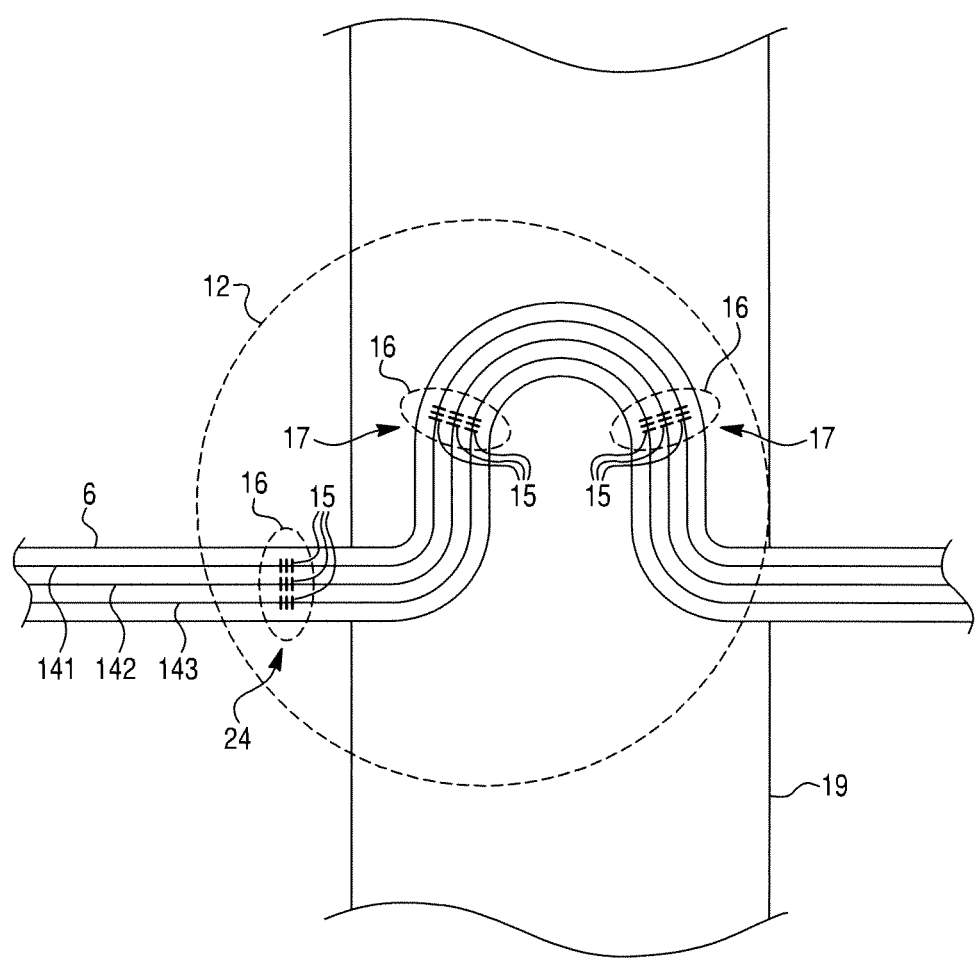
FIG. 7 illustrates a sensing component of an optical fiber in a fiber optic tracking system according to an embodiment of the invention.

FIG. 7 shows in detail an example of a configuration of a sensing component 12 of an optical fiber 6 with a tri-core configuration, i.e., having three cores 141, 142, 143. The sensing component 12 may include sets 16 of optical elements 15. The sets 16 of optical elements 15 may be located at different positions along the optical fiber 6. Each set 16 of optical elements 15 preferably includes an optical element 15 corresponding to each core 141, 142, 143 of the optical fiber 6. The optical elements 15 in a set 16 are preferably positioned proximate one another, and at the same point along the length of the optical fiber 6.

In a preferred embodiment, each optical element 15 is a fiber Bragg grating ("FBG"). A FBG may be fabricated by known techniques, such as by exposing a photosensitive optical fiber to a pattern of pulsed ultraviolet light from a laser, forming a periodic change in the refractive index of a core of the optical fiber. The pattern, or grating, reflects a frequency band of light that is dependent upon the modulation period formed in the core of the optical fiber. However, other types of optical elements 15 may also be used, such as a microbend sensor or an interferometric strain sensor. Microbend sensors are intensity based sensors. Examples of interferometric strain sensors include Fabry-Perot sensors, Michelson sensors, Mach-Zender sensors, and Sagnac sensors. These optical elements 15 produce modified optical signals based on the strain or local bend of the optical fiber 6 or changes thereto.

Each of the sets 16 of optical elements 15 can provide sensing points 17, 24 along the optical fiber 6, which are used to determine the shape of the optical fiber 6 or portions thereof. It is preferred that some of the sets 16 of optical elements 15 are constrained, i.e., fixed relative to the substantially rigid object 19, and other sets 16 of optical elements 15 are unconstrained, i.e., substantially free to move relative to the substantially rigid object 19. The constrained sets 16 of optical elements 15 are referred to herein as fixed sensing points 17, and the unconstrained sets 16 of optical elements 15 are referred to herein as unfixed sensing points 24. Preferably, a sensing component 12 includes at least two fixed sensing points 17.

In order to determine the shape of the optical fiber 6 up to and including a substantially rigid object, all of the sensing points of the optical fiber 6 on the substantially rigid object 19 and between the substantially rigid object 19 and a reference point are used. Thus, the sensing component for a given substantially rigid object 19 can include all of the sensing points of the optical fiber 6 on the substantially rigid object and between the substantially rigid object and the reference point. For example, for the case of the substantially rigid object 19 shown in FIG. 2, the sensing component 12a would include the sensing point 24 to the left of object 19 and the sensing points 17 on the object 19. In the case of substantially rigid object 19', the sensing component 12b would include all three sensing points 24 to the left of object 19' and the sensing points 17 on substantially rigid objects 19 and 19'. In this case, it can be seen that the sensing component 12b used to track the substantially rigid object 19' in FIG. 2 can include the sensing points of the sensing component 12a used to track the substantially rigid object 19.

For reasons that will become apparent from the description below, it is preferred that the portion of the optical fiber 6 having the fixed sensing points 17 (the constrained sets 16 of optical elements 15) will be constrained to have a fixed geometry. It is also preferred that a pose of one of the constrained sets 16 of optical elements 15 has a pose that is different from a pose of the other constrained set 16 of optical elements 15.

Figure 8:
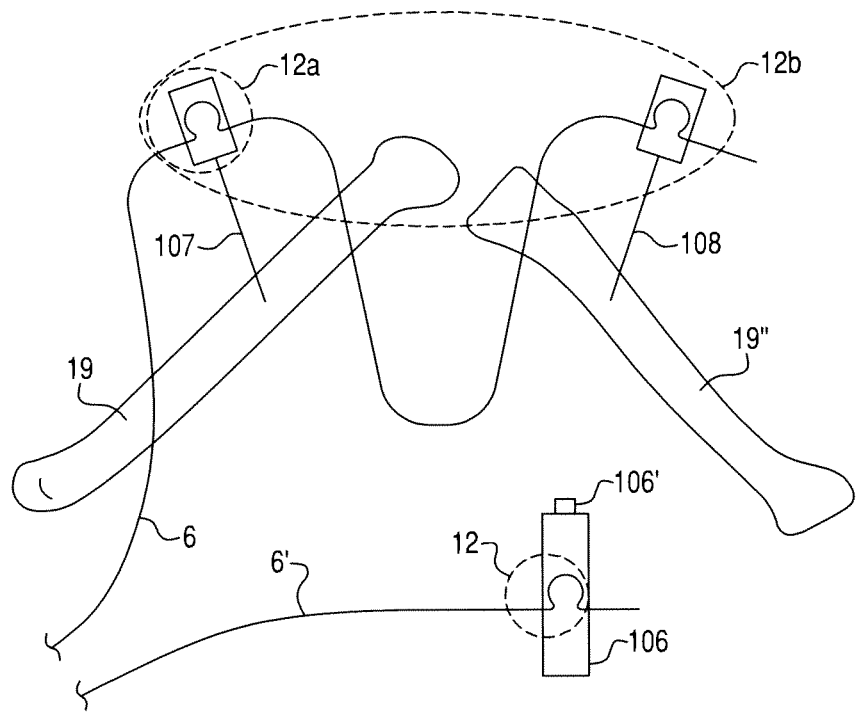
FIG. 8 is a perspective view of an optical fiber of a fiber optic tracking system connected to objects by trackers according to an embodiment of the invention.

At the fixed sensing points 17, the optical fiber 6 can be fixed or attached directly, indirectly, or by a combination thereof, to the substantially rigid object 19 by any available method. For example, direct fixation or attachment can be accomplished using glue, bone screws, and/or clamps that hold the sensing point 17 of the optical fiber 6 against a corresponding location on the substantially rigid object 19. Indirect fixation or attachment can be accomplished by directly attaching the optical fiber 6 to an element that is directly attached to the substantially rigid object 19. As shown in FIG. 8, for example, trackers 107, 108 can be used to fix the position of sensing points 17 of the optical fiber 6 relative to the substantially rigid object 19. The trackers 107, 108 may include metal plates on pins or screws that are attached by conventional means to the substantially rigid object(s) 19, 19", so as to protrude therefrom. Each fixed sensing point 17 is fixed to a portion of a corresponding tracker 107, 108.

When trackers 107, 108 are used for fixation, it is necessary to register the location of each fixed sensing point 17 relative to its corresponding position on the substantially rigid object 19, 19' or to some other point of interest on that substantially rigid object 19, 19'. Such registration can be performed using a probe 106, as described above in connection with FIGS. 4 and 5. For example, a tracked probe can be used to collect points on the surface of the substantially rigid object (relative to the tracker), and a best fit can be calculated between these surface points and a pre-operative CT model. As a further example, an x-ray image intensifier (C-arm or fluoroscope) can be used to capture static 2D images intra-operatively in order to register the tracker to a pre-operative CT model of the substantially rigid object (2D-3D registration). As yet another example, an intra-operative multi-dimensional surgical imaging platform (i.e., O-arm) can be used to reconstruct a 3D model of the substantially rigid object and capture static 2D images to locate the position of the tracker with respect to the substantially rigid object. As yet another example, fiducial markers (e.g., ACUSTAR® or similar markers) could be used during imaging (e.g., CT/MR) to locate the base of the FBG mounting relative to an anatomical coordinate system, which provides for inherent localization of the sensing component and registration of the substantially rigid object.

The Detection Unit

The detection unit 9 can be coupled to the optical fiber 6 by conventional means and configured to detect the modified optical signals from the sensing components 12. For example, the detection unit can be coupled to the optical fiber 6 by means of the optical coupler 25 that couples optical signal from the optical fiber 6 to an optical fiber 6a. In turn, the optical signals are transmitted via the optical fiber 6a to the detection unit 9. Using conventional technology, the detection unit 9 can be configured to distinguish which modified optical signals come from which sensing components 12 and, more particularly, which modified signals come from which optical elements 15. The detection unit 9 also can be configured to detect a difference between (1) the modified optical signals and (2) the optical signals from the light source 7 or some other reference information. The detection unit 9 may comprise, for example, a conventional reflectometer, such as a frequency domain reflectometer.

The Calculation Unit

By performing calculations based on the detected, modified optical signals, the calculation unit 3 can be configured to determine (1) the pose of the substantially rigid object 19 and/or (2) the relative angle between two substantially rigid objects 19, 19", as will be explained in more detail below. Moreover, the calculation unit 3 can be configured to detect a difference between (1) the modified optical signals and (2) the optical signals from the light source 7 or some other reference information, if such detection does not occur in the detection unit 9. The calculation unit 3 may be, for example, a computer.

It is to be understood that the detection unit 9 and the calculation unit 3 need not be physically separate devices. Instead, they may be contained within the same housing or structure.

Using the Fiber Optic Tracking System to Track or Determine the Pose or Angle of an Object In general, according to the present invention, the pose of a substantially rigid object 19 in six degrees of freedom (6D pose) or relative angles can be determined by (1) knowing or determining the shape of the optical fiber 6 or portions thereof and (2) knowing or determining the spatial relationship between substantially rigid objects 19 and the optical fiber 6.

The shape (position coordinates and fiber orientation) of the optical fiber 6 may be determined by determining the local fiber bend at multiple sensing points 17, 24 along the optical fiber 6. The sensing components 12 located at each of the sensing points 17, 24 provide modified optical signals, which correspond to the strain in the optical fiber 6 at those points. In particular, the strain in the optical elements 15, such as FBGs, of the sensing components 12 may be determined based on the frequency distribution of return signals (the modified optical signals) from each of the FBGs. In general, a change in spacing of the grating of a FBG will depend on the strain, and thus the frequency distribution of its modified optical signal will depend on the strain. Because the strain provides an indication of the local fiber bend at those points, the detection unit 9 and the calculation unit 3 can use the modified optical signals to determine the local fiber bend at the sensing points 17, 24 and thus determine the shape of the optical fiber 6 or pertinent portions thereof. A specific example of how the shape of the optical fiber 6 can be reconstructed based on differential strain measurement at each sensing point 17 and from sensing points 24 is disclosed, for example, in United States Patent Application Pub. No. 2007/0065077, published Mar. 22, 2007, which is incorporated by reference herein in its entirety.

The spatial relationship between the substantially rigid object 19 and the optical fiber 6 can be known or determined by fixing the substantially rigid object 19 relative to the optical fiber 6. More particularly, two or more fixed sensing points 17 of the optical fiber 6 are fixed relative to the corresponding substantially rigid object 19, as was previously described. To use the fixed sensing points 17 to determine the spatial relationship between the substantially rigid object 19 and the optical fiber 6, the fiber orientation or direction for at least two of the fixed sensing points 17 should be non-collinear, Providing two or more fixed sensing points 17 with non-collinear fiber orientations provides a clear understanding of the spatial relationship between the substantially rigid object 19 and the optical fiber 6. If, to the contrary, the fiber orientation of the fixed sensing points 17 are collinear, pose of the substantially rigid object 19 cannot be determined. As an aside, it is not necessary to initially know which of the sensing points 17, 24 are fixed sensing points 17, as that can be determined through operation. In particular, by tracking the movement of the sensing points 17, 24, it may be determined which of them are fixed sensing points 17 (they exhibit no change in the modified optical signals) and which are unfixed sensing points 24 (they exhibit change in the modified optical signals).

Figure 9:
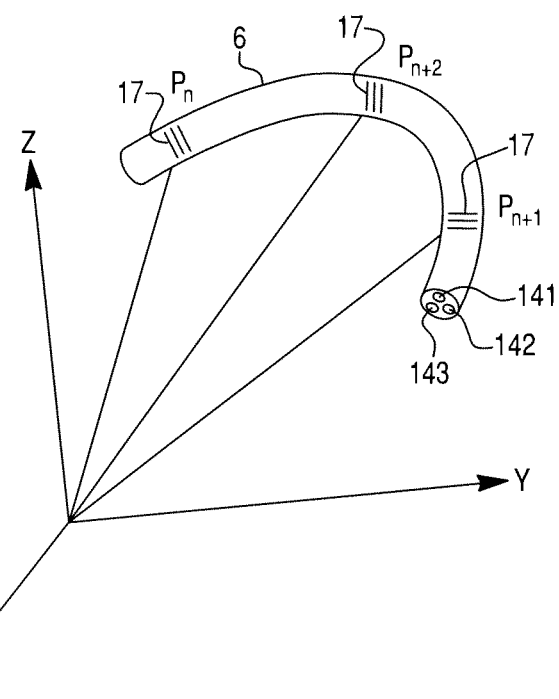
FIG. 9 illustrates an optical fiber with three sensing points according to an embodiment of the invention.

For illustration purposes, FIG. 9 shows a non-collinear arrangement of points $p_n$, $p_{n+1}$, and $p_{n+2}$, which correspond to fixed sensing points 17 along a tri-core optical fiber 6 (having three cores 141, 142, 143). Using only two non-collinear fixed sensing points 17 (e.g., $p_n$, and $p_{n+1}$), the 6D pose may be determined based on the position coordinates of those points and the fiber orientation, i.e., the direction of the optical fiber at those points. Using three or more non-collinear fixed sensing points 17 (e.g., $p_n$, $p_{n-1}$, and $p_{n+2}$), the 6D pose may be determined merely based on the position coordinates of those points.

Figure 10:
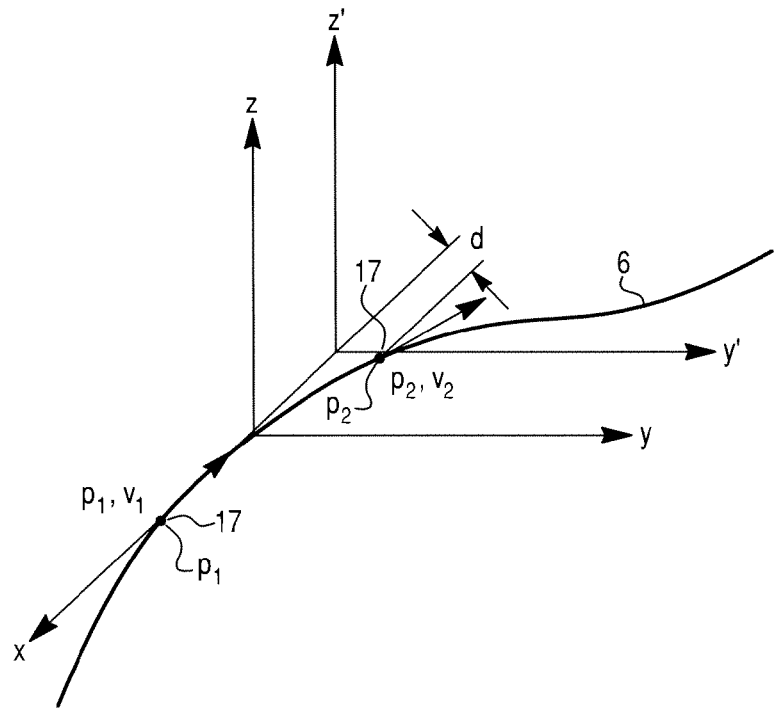
FIG. 10 illustrates an optical fiber with two non-collinear fixed sensing points according to an embodiment of the invention.

FIG. 10 illustrates an embodiment for determining the 6D pose where the pose is determined based on only two non-collinear fixed sensing points 17 (namely $p_1$ and $p_2$) of the optical fiber 6, where the optical fiber 6 is in a fixed geometry between the two points. Though not shown, it is to be understood that the fixed sensing points 17 are fixed (directly or indirectly) to a substantially rigid object 19. As shown in FIG. 10, the $p_i$'s are position vectors to the points and $v_i$'s are fiber orientation vectors at the points. The fiber orientation vectors provide the direction of a tangent to the optical fiber 6 at the points. To determine the 6 degrees of freedom (DOF) of the coordinate system containing $p_1$ and $p_2$ and the substantially rigid object 19, three rotation directions may be determined. The first rotation direction comes from $v_1$. The second rotation direction can be determined from calculating the cross product of $v_2$ and $v_1$, e.g., $[v_1 \times v_2]$. The cross product of $v_2$ and $v_1$ equals $v_3$, known as the resultant vector, which is the second rotation direction. By forming the cross product of the resultant vector with $v_1$, a fourth vector $v_4$, that is mutually orthogonal to $v_1$ and $v_3$, is created. The third rotation direction is thus determined as the fourth vector $v_4$. Thus, a 6 DOF coordinate system is determined and can be used to establish a 6D pose of the substantially rigid object 19. Specifically, by tracking $p_1$, $v_1$, $p_2$, and $v_2$, the 6D pose of the substantially rigid object 19 attached to the optical fiber 6 is established and can thus be tracked.

Figure 12:
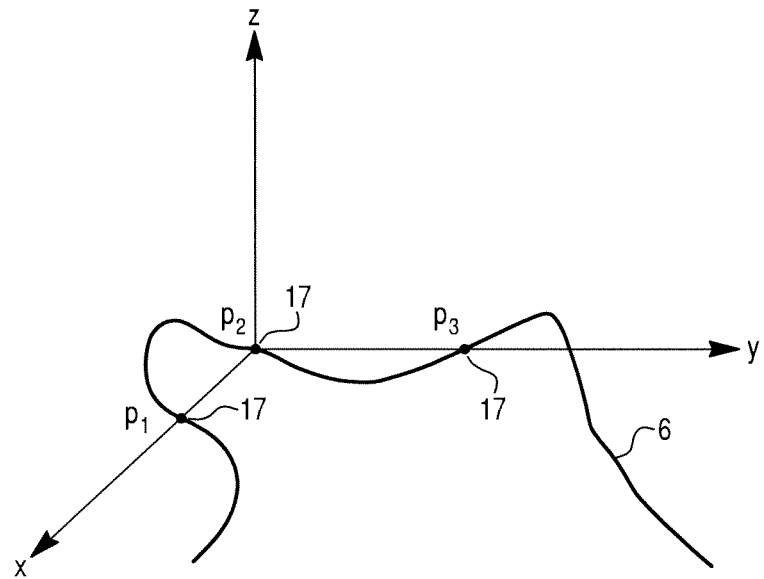
FIG. 12 illustrates an optical fiber with three non-collinear fixed sensing points according to an embodiment of the invention.

FIG. 12 illustrates an embodiment for determining the 6D pose where the pose is determined based on at least three non-collinear fixed sensing points 17 (namely, $p_1$, $p_2$ and $p_3$). Though not shown, it again is to be understood that the fixed sensing points 17 are fixed (directly or indirectly) to a substantially rigid object 19. In such a configuration, the 6D pose may be determined merely based on the position coordinates of those points $p_1$, $p_2$ and $p_3$. Three examples of techniques for doing so are described below.

A first technique for determining the 6D pose based on the position coordinates involves use of basis vectors. In particular, the 6D pose may be determined by defining basis vectors based on the coordinates of the three fixed sensing points 17 ($p_1$, $p_2$ and $p_3$). The basis vectors are determined in terms of the position vectors of the three points, $p_1$, $p_2$, and $p_3$. For example, $$\vec{v}_1 = \vec{p}_2 - \vec{p}_1, \vec{v}_2 = \vec{p}_3 - \vec{p}_1, \vec{x} = \frac{\vec{v}_1}{|\vec{v}_1|}, \vec{y} = \frac{\vec{v}_1 \times \vec{v}_2}{|\vec{v}_1 \times \vec{v}_2|}, \text{ and } \vec{z} = \vec{x} \times \vec{y}.$$

It should be noted that only the position vectors, and not the orientation vectors, of the fixed sensing points need be used in determining the pose in this fashion.

A second technique for determining the 6D pose based on the position coordinates involves use of a least squares method. In particular, the 6D pose may be determined by constraining the three fixed sensing points 17 ($p_1$, $p_2$ and $p_3$) to lie along a portion of the optical fiber 6 having a fixed geometry, such as to lie in a plane, and to use a least squares method for fitting to the fixed geometry. Increasing the number of fixed sensing points 17 can reduce the uncertainty for the least squares method, and this increase in the number of fixed sensing points 17 can be exploited statistically to reduce the uncertainty of the 6D pose estimate.

A third technique for determining the 6D pose based on the position coordinates involves use of point cloud registration. In particular, the 6D pose may be determined using a point cloud registration between an apriori model of the points in a local coordinate system and measured points Exemplary methods for such a point cloud registration, are described, for example, in the articles F.E. Veldpaus et al., *A Least-Squares Algorithm for the Equiform Transformation from Spatial Marker Co-ordinates*, J. Biomechanics Vol. 21, No. 1, pp. 44-54(1988), which describes an eigenvector/eigenvalue method; and John H. Challis, *A Procedure for Determining Rigid Body Transformation Parameters*, J. Biomechanics, Vol. 28, No. 6, pp. 733-737 (1995), which describes an SVD method, both of which articles are incorporated herein by reference.

In the above-described processes for determining the 6D pose, increasing the number of fixed sensing points 17 $p_i$, may increase the accuracy of the pose estimate when the point estimates are unbiased. For an uncertainty $\epsilon_i$ associated with the measurement system, the coordinates of any particular point $p_i$ can be known within some error (e.g., $p_i + \epsilon_i$). The point estimates are unbiased when the mean of the error $\epsilon_i$ is zero. While the uncertainty for a given point $p_i$ may remain the same regardless of the number of fixed sensing points 17, the uncertainty for the 6D pose will in general decrease in response to an increase in the number of fixed sensing points 17. As a particular example, with regard to the least squares method, as the number of fixed sensing points 17 used in determining the 6D pose increases, the overall uncertainty in the pose will decrease and for unbiased point estimates of points $p_i$, overall accuracy is increased.

In the above-described processes for determining the 6D pose, while the fixed sensing points 17 of the optical fiber 6 should be fixed to the substantially rigid object 19, it is not required that the portions of optical fiber 6 between the fixed sensing points 17 be fixed to the substantially rigid object 19 or that they be fixed in a particular geometry. Rather, the portions of the optical fiber 6 between the fixed sensing points 17 may be unfixed, and the 6D pose may still be determined.

However, constraining a portion of the optical fiber 6 between the fixed sensing points 17 to have known shape or positions at certain points or portions will increase the accuracy of the pose estimate. That is, by increasing the number of known positions along the optical fiber 6, the accuracy of the overall shape determination can be increased. Consequently, the accuracy of the pose estimate based on the fiber shape determination also can be increased.

The optical fiber 6 may be constrained to have known positions at certain points or portions in a number of ways. For example, an entire portion of the optical fiber 6 containing the fixed sensing points 17 can be constrained to have a fixed geometry, which can be fixed relative to the substantially rigid object 19. Several geometries for constraining the optical fiber 6 may be used. For example, a planar arc or planar loop (e.g., a circle) may be used. As another example, the ending point of the optical fiber 6 relative to the beginning point may be known.

Figure 11:
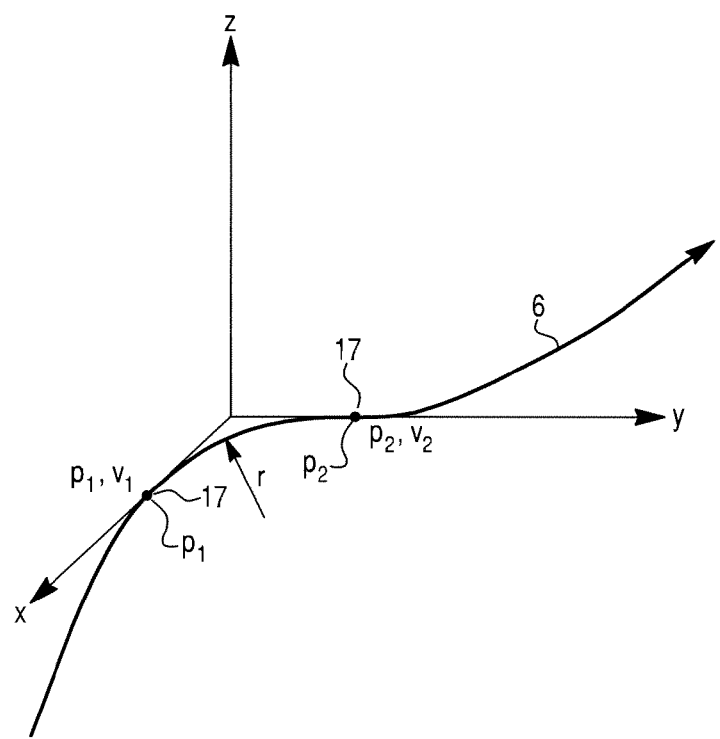
FIG. 11 illustrates an optical fiber in a constrained geometric shape according to an embodiment of the invention.

FIG. 11 illustrates an embodiment where the fixed sensing points 17 ($p_1$ and $p_2$) are on a portion of the optical fiber 6 that is constrained to follow a fixed geometry, in this case a planar arc. The vectors $v_1$ and $v_2$ are constrained to lie in the same plane, while the points $p_1$ and $p_2$ are constrained to be points on the fixed geometry. The 6D pose and the coordinate system transformation can be obtained from the cross products of $v_1$ and $v_2$, in a way similar to the calculation of the coordinate system transformation described in relation to FIG. 10.

Figure 13:
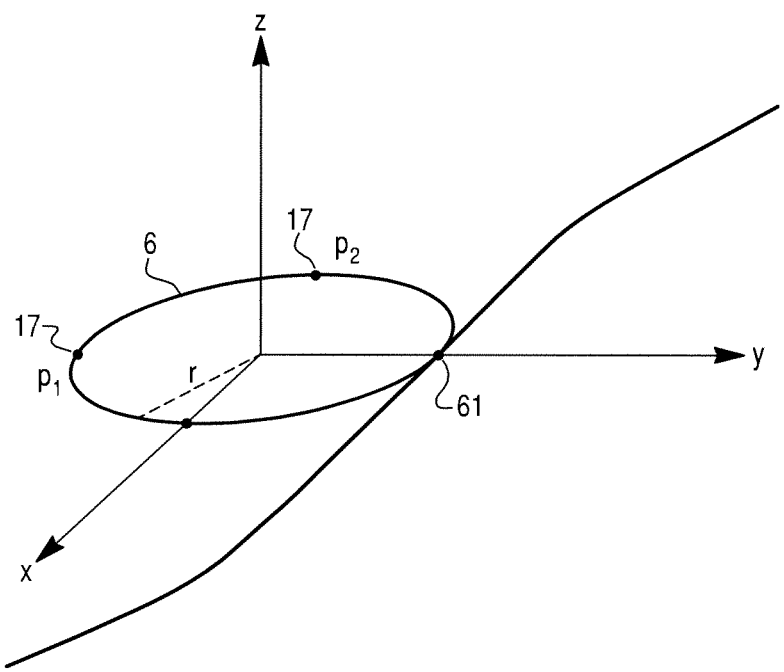
FIG. 13 illustrates an optical fiber in a constrained geometric shape according to an embodiment of the invention.
Figure 14:
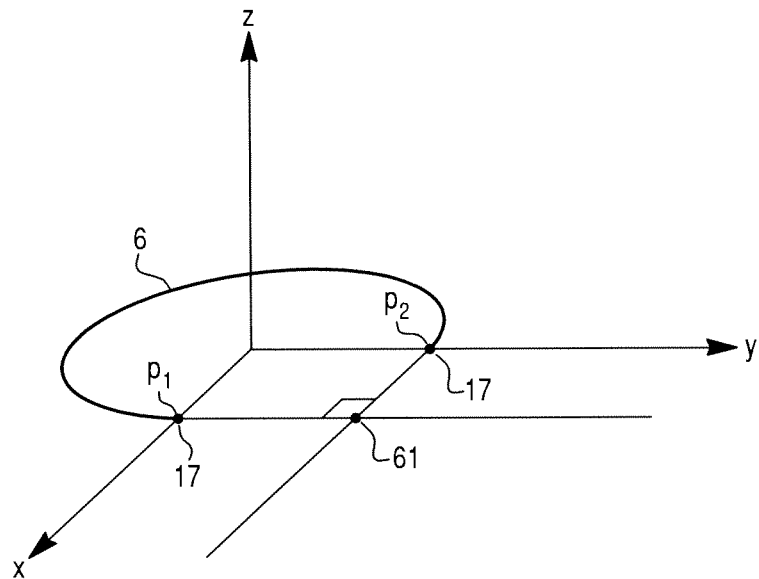
FIG. 14 illustrates an optical fiber in a constrained geometric shape according to an embodiment of the invention.

In yet another embodiment, a constraint such as a planar loop, as shown in FIGS. 13 and 14, may be used to identify the points of attachment of the optical fiber 6 along the substantially rigid object, where the fixed sensing points 17 ($p_1$ and $p_2$) are on the loop. Preferably the loop has a bend that is near the minimum bend radius $r_{min}$ of the optical fiber 6. Minimizing the size of the loop provides for a more convenient measuring system. The bend of the loop, however, need not be near the minimum bend radius $r_{min}$. In the case of such a loop, the crossing point 61 of the loop (i.e., the point at which the optical fiber 6 intersects itself) can be fixed. FIG. 14 illustrates an embodiment wherein a right angle is defined at the crossing point 61, while in FIG. 13 a 180 degree angle is defined. The optical fiber loop provides a convenient way to fix points along that portion of the optical fiber 6. Because the loop has a fixed geometry, the optical fiber 6 always crosses at the crossing point 61. The crossing point 61 can be used to reduce noise in the fiber shape measurement, and thus the 6D pose measurement, because the crossing point is known to remain fixed. The 6D pose may be determined in a similar fashion to the embodiments described with respect to FIGS. 10 and 11, i.e., using the position and orientation vectors of two fixed sensing points.

Figure 15:
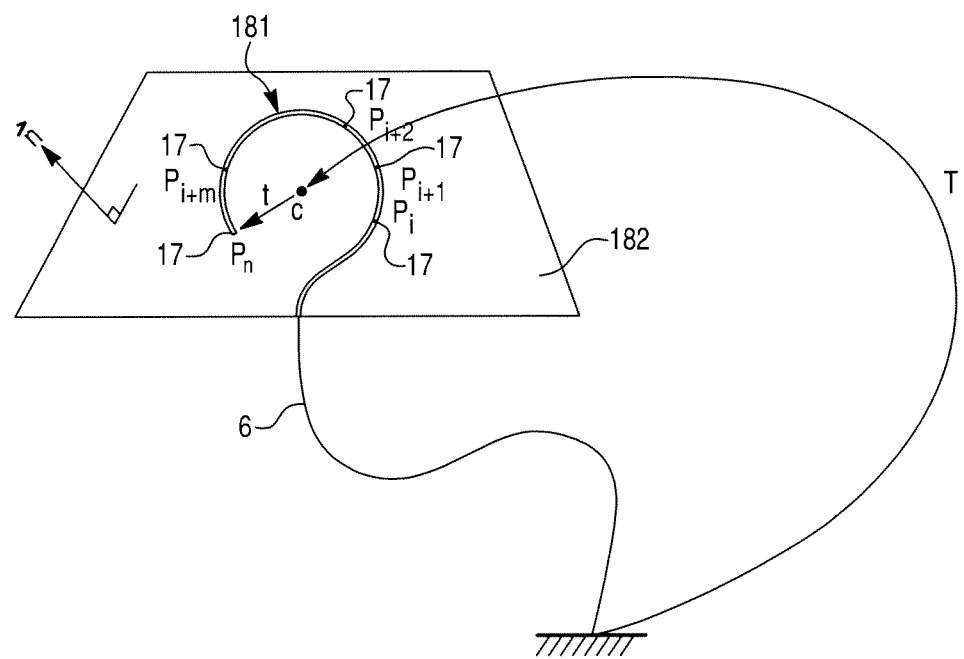
FIG. 15 illustrates an optical fiber in a constrained geometric shape according to an embodiment of the invention.

FIG. 15 illustrates an embodiment where a portion of the optical fiber 6 is constrained to have a fixed geometry, namely to follow a groove 181 in a tracker plane 182. The portion of the optical fiber 6 constrained in the groove 181 includes n fixed sensing points 17 ($p_i$, $p_{i+1} \ldots p_{i+n}$, $p_n$). To determine the 6D pose, the plane in which the constrained part of the optical fiber 6 resides may be identified. The plane may be represented by a point $\vec{p}$, and the plane normal vector, where the plane normal vector is represented by the equation $\vec{n} = [n_x, n_y, n_z]$ where n is a function of the position of the fixed sensing points 17 in the portion of the optical fiber 6 constrained to follow the groove 181 as $\vec{n} = f(p_1, p_{i+1} \ldots p_{i+n}, p_n)$. The plane can be expressed by the equation $n_x x + n_y y + n_z z + d = 0$. The unknowns in the plane equation can be determined from a set of three or more non-collinear points using the linear system of equations:

$$\begin{bmatrix} x_1 & y_1 & z_1 & 1 \\ x_i & y_i & z_i & 1 \\ \vdots & \vdots & \vdots & \vdots \\ x_n & y_n & z_n & 1 \end{bmatrix} \begin{bmatrix} n_x \\ n_y \\ n_z \\ d \end{bmatrix} = 0.$$

The points $p_i$ to $p_n$ are projected onto the plane so that the center C of the circular arc can be determined. The tangent vector $\vec{t}$ is determined from the equation $$\vec{t} = \frac{P_n - C}{\|P_n - C\|}.$$

The transformation matrix, which provides the transformation from one coordinate system to another, and which thus provides the 6D pose, can be constructed from the normal and tangent vectors as $$T = \begin{bmatrix} \vec{n} & \vec{t} & \vec{n} \times \vec{t} & \vec{p} \\ 0 & 0 & 0 & 1 \end{bmatrix}.$$

The transformation matrix provides linear translation as well as angular rotation from one coordinate system to another, as in known in the art, and thus provides the 6D pose.

Figure 16A:
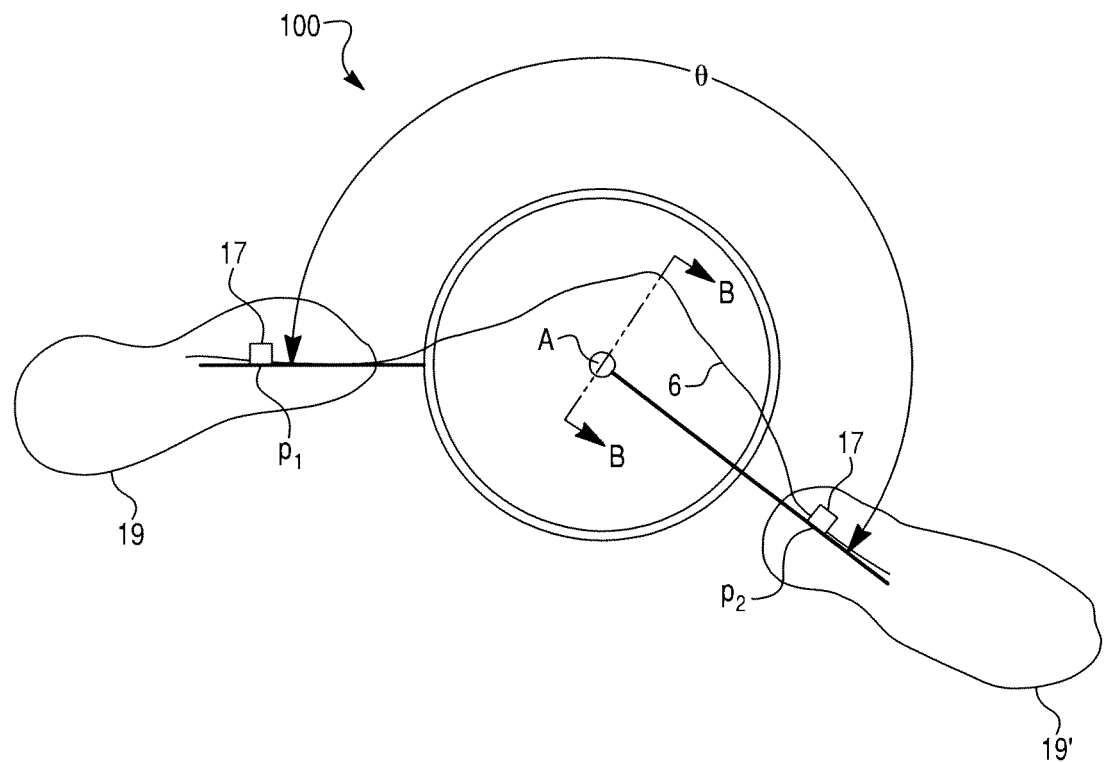
FIG. 16A is a view of a fiber optic tracking system serving as an angular transducer according to an embodiment of the invention.
Figure 16B:
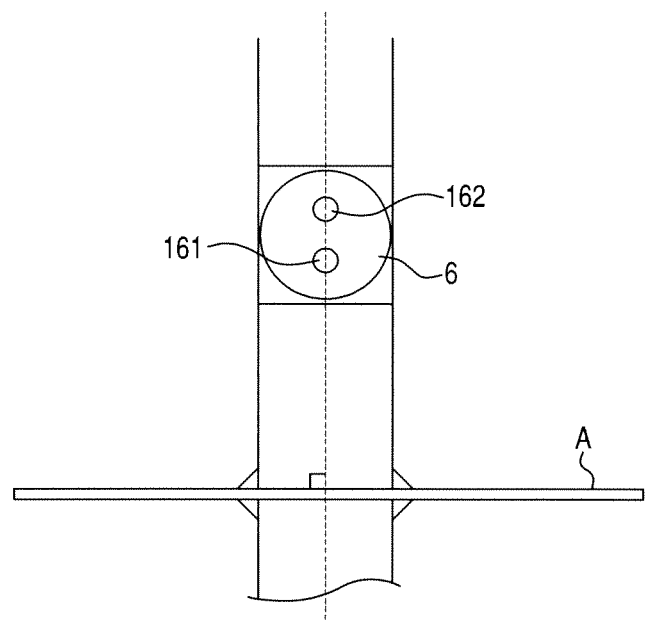
FIG. 16B is a cross-section view of a portion of the fiber optic tracking system of FIG. 16A illustrating the relative arrangement of the cores of the optical fiber of the system.

FIGS. 16A and 16B illustrate an embodiment of the fiber optic tracking system 100, in which it acts as an angular transducer that can determine the angle between a first substantially rigid object 19 and a second substantially rigid object 19'. In this embodiment, the fixed sensing points 17 ($p_1$ and $p_2$) are fixed to the first and second substantially rigid objects 19, 19', respectively, where the substantially rigid objects 19, 19' are constrained to rotate relative to each other in one dimension about a rotation axis A to define an angle θ. It should be noted that the portion of the optical fiber 6 between the fixed sensing points 17 need not follow a constrained path. Acting as an angular transducer, the fiber optic tracking system 100 is used to measure that angle θ.

As can be seen in FIG. 16B, which is a cross section of a portion of the tracking system 100 along a line B-B in FIG. 16A, the fiber optic tracking system 100 may include a dual-core optical fiber 6 having two cores 161, 162, where the two cores are aligned perpendicular to the rotation axis A. The two cores are oriented to lie in the plane perpendicular to the rotation axis A, where the core 162 is radially further away from the rotation axis A than the core 161.

The angle θ is determined by transducing the relative strain between the two cores of the optical fiber 6. The orientation vectors at the entrance and exit of the joint, i.e., at points $p_1$ and $p_2$, can be used to determine the joint angle θ. Specifically, the equation $$\theta = \cos^{-1}\left(\frac{\vec{v}_1 \cdot \vec{v}_2}{|\vec{v}_1||\vec{v}_2|}\right)$$

can be used to determine the angle θ, where $v_1$ and $v_2$ are the orientation vectors at points $p_1$ and $p_2$, respectively. Thus, the angle θ between the first substantially rigid object 19 and the second substantially rigid object 19' can be obtained.

While FIGS. 16A and 16B illustrate the fiber optic tracking system 100 serving as a single angular transducer for determining a relative rotation angle between two substantially rigid objects 19, 19', in general it can serve as multiple angular transducers in a system having three or more substantially rigid objects, where pairs of the substantially rigid objects are constrained to rotate relative to each other in one dimension. In this case, an angular transducer would be coupled to each substantially rigid object pair to determine the relative angle between the objects of the pair. Such a system can be configured to determine a 6D pose.

Figure 17:
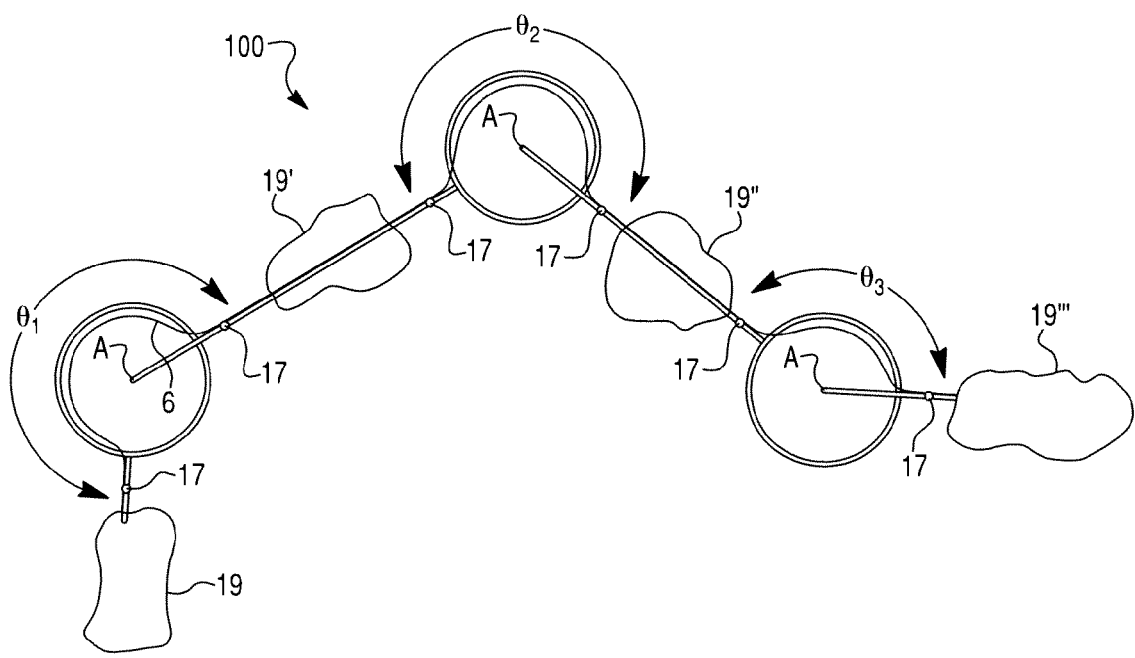
FIG. 17 is a view of a fiber optic tracking system serving as a multiple angular transducer according to an embodiment of the invention.

FIG. 17 illustrates such an embodiment of the fiber optic tracking system in a system 100 having four substantially rigid objects 19, 19', 19" and 19''', where the system can transduce the angle between pairs of the substantially rigid objects. Namely, the system 100 in FIG. 17 can transduce the angle $θ_1$ between objects 19 and 19' of a first pair, the angle $θ_2$ between objects 19' and 19" of a second pair, and the angle $θ_3$ between objects 19" and 19''' of a third pair. It should be noted that while FIG. 17 illustrates the rigid objects all constrained to move in a same plane, this is not a requirement.

The angles $θ_1$, $θ_2$, and $θ_3$ may be determined in a similar fashion to that described above with respect to FIGS. 16A and 16B for a single angular transducer. In that regard, each pair of substantially rigid objects has fixed sensing points 17 of the optical fiber 6 respectively fixed to objects of the pair. The angles about the rotation axis A of a pair may be determined using orientation vectors as discussed above with respect to FIGS. 16A and 16B.

Temperature Compensation

Fluctuation in temperature is a source of potential inaccuracy in the tracking performed by the fiber optic tracking system 100. For example, the strain in a FBG in conventional optical fiber is sensitive to temperature, as well as the local fiber bend. To accurately track the substantially rigid object 19, it is preferable to address the potential effect of temperature fluctuation.

The potential inaccuracy caused by temperature fluctuation can be addressed by removing temperature as a variable. For example, the temperature of the environment of the fiber optic tracking system 100 can be maintained constant.

Figure 18:
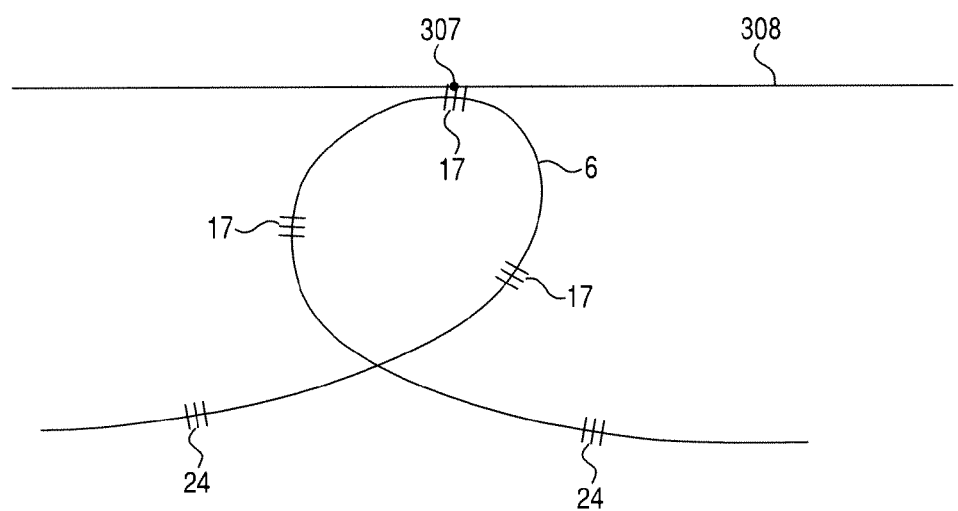
FIG. 18 is a view of a fiber optic tracking system configured for temperature compensation according to an embodiment of the invention.

Alternatively, the potential inaccuracy can be addressed by compensating for temperature fluctuations. The change $\Delta\lambda_B$ in the wavelength of light reflected by a FBG relative to a wavelength $\lambda_B$ at temperature T is provided by the equation $\Delta\lambda_B = \lambda_B(\alpha_A + \alpha_n)\Delta T$, where $\alpha_A$ is the thermal expansion coefficient of the optical fiber, $\alpha_n$ is the thermo-optic coefficient, and $\Delta T$ is the change in temperature. Therefore, to obtain a more accurate local fiber bend estimate, temperature may be measured along the optical fiber 6 that is used to track the substantially rigid object 19, and any temperature fluctuation can be factored into the determination of local fiber bend to reduce or eliminate any inaccuracy. As shown in FIG. 18, temperature fluctuation may be measured along the optical fiber 6 by, for example, providing an additional optical fiber 308 having a FBG 307, which will sense a strain change resulting from only temperature fluctuation. To ensure that the strain change results from only temperature fluctuation, the strain measured by the FBG 307 must be measured at a point along the optical fiber 308 that does not experience a change in its local fiber bend. Similar compensation for temperature fluctuation also can be accomplished using other sensors of temperature fluctuation, such as a thermocouple, for example.

Other embodiments of the invention will be apparent to those skilled in the art from consideration of the specification and practice of the invention disclosed herein. It is intended that the specification and examples be considered as exemplary only.

What is claimed is:

1. A fiber optic tracking system for tracking a substantially rigid object, comprising:
   a light source that provides optical signals;
   an optical fiber having a sensing component configured to modify optical signals from the light source, the optical fiber being configured to attach to the substantially rigid object;
   a detection unit arranged to receive the modified optical signals from the sensing component; and
   a calculation unit configured to determine a pose of the substantially rigid object in six degrees of freedom based on the modified optical signals,
   wherein the sensing component includes at least a first set of optical elements comprising a first sensing point and a second set of optical elements comprising a second sensing point, wherein the first and second sensing points are separated at a distance along the optical fiber, and
   wherein a position and orientation of the first set of optical elements is fixed relative to a position and orientation of the second set of optical elements and the positions and orientations of the first and second sets of optical elements are fixed with non-collinear fiber orientations relative to the same substantially rigid object.

2. The fiber optic tracking system of claim 1, wherein the substantially rigid object includes at least one of a portion of a body and an instrument.

3. The fiber optic tracking system of claim 1, wherein the optical fiber includes at least one of a multi-core fiber and a plurality of single core fibers.

4. The fiber optic tracking system of claim 1, wherein the optical fiber is configured to at least one of attach directly to the substantially rigid object and attach to an element that is attached directly to the substantially rigid object.

5. The fiber optic tracking system of claim 1, wherein at least one of the detection unit and the calculation unit is configured to detect a difference between the optical signals from the light source and the modified optical signals.

6. The fiber optic tracking system of claim 1, wherein one of the first and second sets of optical elements include at least one of a fiber Bragg grating, microbend sensor, and an interferometric sensor.

7. The fiber optic tracking system of claim 1,
   wherein a portion of the optical fiber that includes the first and second set of optical elements is constrained to have a fixed geometry.

8. The fiber optic tracking system of claim 7, wherein the pose of the substantially rigid object in six degrees of freedom is determined based at least in part on a location of the first set of optical elements, a first vector along a direction of the optical fiber at the location of the first set of optical elements, and a second vector along a direction of the optical fiber at a location of the second set of optical elements.

9. The fiber optic tracking system of claim 7, wherein the portion of the optical fiber that includes the first and second set of optical elements is constrained to have a predetermined geometry.

10. The fiber optic tracking system of claim 9, wherein the predetermined geometry includes at least one of a planar arc and a planar loop.

11. The fiber optic tracking system of claim 10, wherein the planar loop has a constant radius.

12. The fiber optic tracking system of claim 10, wherein the planar loop includes a fixed crossing point where a first point on the optical fiber overlaps a second point on the optical fiber.

13. The fiber optic tracking system of claim 7, wherein the first and second set of optical elements are disposed on a plane perpendicular to an axis of revolution of a joint of the substantially rigid object.

14. The fiber optic tracking system of claim 1, wherein the sensing component includes at least three sets of optical elements, and wherein the optical fiber is constrained such that positions of the three sets of optical elements are non-collinear.

15. The fiber optic tracking system of claim 14, wherein the calculation unit is configured to calculate the pose based on basis vectors determined from positions of the at least three sets of optical elements.

16. The fiber optic tracking system of claim 14, wherein the calculation unit is configured to calculate the pose based on a least squares fit method using the positions of the at least three sets of optical elements.

17. The fiber optic tracking system of claim 14, wherein the calculation unit is configured to calculate the pose based on a point cloud registration method using the positions of the at least three sets of optical elements.

18. The fiber optic tracking system of claim 1, wherein the optical fiber has a second sensing component configured to modify optical signals from the light source to provide second modified optical signals, the optical fiber being configured to attach to a second substantially rigid object;
   the detection unit is arranged to receive the second modified optical signals from the second sensing component; and
   the calculation unit is configured to determine a pose of the second substantially rigid object in six degrees of freedom based on the second modified optical signals.

19. A method for tracking a substantially rigid object using a fiber optic tracking system, comprising:
   providing a light source;
   attaching an optical fiber, having a sensing component configured to modify the optical signals from the light source, to the substantially rigid object, wherein the sensing component includes at least a first set of optical elements comprising a first sensing point and a second set of optical elements comprising a second sensing point, wherein the first and second sensing points are separated at a distance along the optical fiber;
   constraining the optical fiber such that a position and orientation of the first set of optical elements is fixed relative to a position and orientation of the second set of optical elements and the positions and orientations of the first and second sets of optical elements are fixed with non-collinear fiber orientations relative to the same substantially rigid object; and
   determining a pose of the substantially rigid object in six degrees of freedom based on the modified optical signals.

20. The method of claim 19, further comprising:
   at least one of attaching the optical fiber directly to the substantially rigid object and attaching the optical fiber directly to an element that is attached directly to the substantially rigid object.

21. The method of claim 19, further comprising:
   determining the pose of the substantially rigid object in six degrees of freedom based at least in part on a location of the first set of optical elements, a first vector along a direction of the optical fiber at the location of the first set of optical elements, and a second vector along a direction of the optical fiber at the location of the second set of optical elements.

22. The method of claim 19, further comprising:
constraining a portion of the optical fiber that includes the first set of optical elements and the second set of optical elements to have a fixed geometry.

23. A computer program product embedded on a non transitory computer readable medium storing a program for tracking a substantially rigid object using a fiber optic tracking system, which when executed by a computer performs a method comprising:
determining a pose of the substantially rigid object in six degrees of freedom based on modified optical signals received from a sensing component of an optical fiber attached to the substantially rigid object,
wherein the sensing component includes at least a first set of optical elements comprising a first sensing point and a second set of optical elements comprising a second sensing point, wherein the first and second sensing points are separated at a distance along the optical fiber, and
wherein a position and orientation of the first set of optical elements is fixed relative to a position and orientation of the second set of optical elements and the positions and orientations of the first and second sets of optical elements are fixed with non-collinear fiber orientations relative to the same substantially rigid object.

24. The computer program product of claim 23, further comprising:
determining the pose of the substantially rigid object in six degrees of freedom based at least in part on a location of the first set of optical elements in the optical fiber, a first vector along a direction of the optical fiber at the location of the first set of optical elements, and a second vector along a direction of the optical fiber at a location of the second set of optical elements in the optical fiber.

25. The computer program product of claim 23,
wherein a portion of the optical fiber that includes the first and second sets of optical elements is constrained to have a fixed geometry.

* * * * *